(12) United States Patent
Rubin (10) Patent No.: US 10,365,204 B2
(45) Date of Patent: Jul. 30, 2019

(54) LONG PATH CELL (71) Applicant: Tom Rubin, Berlin (DE)

(72) Inventor: Tom Rubin, Berlin (DE)

(*) Notice: Subject to any disclaimer, the term of this patent is extended or adjusted under 35 U.S.C. 154(b) by 0 days.

(21) Appl. No.: 16/077,490

(22) PCT Filed: Feb. 9, 2017

(86) PCT No.: PCT/EP2017/052892
§ 371 (c)(1),
(2) Date: Aug. 13, 2018

(87) PCT Pub. No.: WO2017/137502
PCT Pub. Date: Aug. 17, 2017

(65) Prior Publication Data
US 2019/0049364 A1 Feb. 14, 2019

(30) Foreign Application Priority Data

Feb. 11, 2016 (DE) .................. 10 2016 102 430
Feb. 11, 2016 (DE) .................. 10 2016 102 431

(51) Int. Cl.
G01N 1/10 (2006.01)
G01N 21/03 (2006.01)
(Continued)

(52) U.S. Cl.
CPC ....... G01N 21/031 (2013.01); G01N 21/3504 (2013.01); G02B 5/09 (2013.01); G02B 5/10 (2013.01); G02B 7/182 (2013.01); G02B 17/004 (2013.01); G01N 21/31 (2013.01); G01N 2021/0314 (2013.01); G01N 2201/066 (2013.01); G01N 2201/0668 (2013.01); G02B 6/42 (2013.01)

(58) Field of Classification Search
CPC ...... G01N 30/74; G01N 21/031; G01N 21/05; G01N 21/03; G01N 21/0303

USPC .......................................... 356/246
See application file for complete search history.

(56) References Cited

U.S. PATENT DOCUMENTS 4,783,158 A * 11/1988 Shackman ......... G02B 17/0605
359/364
5,471,346 A * 11/1995 Ames ................ G02B 17/0808
359/364
2012/0307328 A1* 12/2012 Kessler ............... G02B 17/008
359/202.1

* cited by examiner

Primary Examiner — Md M Rahman
(74) Attorney, Agent, or Firm — JMB Davis Ben-David (57) ABSTRACT The invention relates to a long path cell (10), in particular a Herriott cell, with (a) a primary mirror (12) and (b) a secondary mirror (14). According to the invention, it is provided that the primary mirror (12) has a first primary mirror segment (42.1) and at least one second primary mirror segment (42.2), which radially surrounds the first primary mirror segment (42.1), whereby the primary mirror segments (42) differ in their curvatures (R42.1, 42.2) or focal lengths, the secondary mirror (14) has a first secondary mirror segment (44.1) and at least one second secondary mirror segment (44.2) which radially sur-rounds the first secondary mirror segment (44.1), whereby the secondary mirror segments (44) differ in their curvatures (R42.1, R42.2) or focal lengths, the first primary mirror segment (42.1) and the first secondary mirror segment (44.1) are arranged in relation to each other such that a light beam is reflected back and forth between the two, and that the second primary mirror segment (42.2) and the second secondary mirror segment (44.2) are arranged in relation to each other such that a light beam is reflected back and forth between the two.

16 Claims, 10 Drawing Sheets (51) Int. Cl.
G01N 21/3504 (2014.01)
G02B 17/00 (2006.01)
G02B 5/09 (2006.01)
G02B 5/10 (2006.01)
G02B 7/182 (2006.01)
G01N 21/31 (2006.01)
G02B 6/42 (2006.01)

LONG PATH CELL

CROSS-REFERENCE TO RELATED APPLICATIONS

This is the U.S. National Stage of International Patent Application No. PCT/EP2017/052892 filed Feb. 9, 2017, which was published in German under PCT Article 21(2), and which in turn claims the benefit of German Patent Application Nos. 10 2016 102 430.9 and 10 2016 102 430.9, both of which filed Feb. 11, 2016.

The invention relates to a long path cell. A long path cell is used in spectroscopy, for example, in order to send a light beam on the longest path possible through a sample volume, so that the interaction between the light beam and the material in the sample chamber is particularly intensive.

A generic long path cell is known from U.S. Pat. No. 9,250,175 B1, in which one of the mirrors consists of a first and a second mirror segment, as a result of which the number of reflections can be increased.

In US 2011/0164251 A1, a generic long path cell is described in which a second reflection pattern is generated by means of a deflection mirror.

A long path cell is known from U.S. Pat. No. 6,486,474 B1 and is used in spectroscopy, for example, in order to send a light beam on the longest path possible through a sample volume, so that the interaction between the light beam and the material in the sample chamber is particularly intensive. It is preferable when, in a particularly simple manner, the long path cell can be inserted into the beam path of a laser, for example.

The long path cell known from US 2011/0164251 A1, in which the light source is arranged within the sample volume, can only be installed into existing systems with difficulty.

The object of the invention is to suggest an improved long path cell. The invention resolves the problem through a long path cell, in particular a Herriott cell, with (a) a primary mirror and (b) a secondary mirror, characterized in that (c) the primary mirror has a first primary mirror segment and at least one second primary mirror segment, which radially surrounds the first primary mirror segment, whereby the primary mirror segments differ in their curvatures or focal lengths, (d) the secondary mirror has a first secondary mirror segment and at least one second secondary mirror segment that radially surrounds the first secondary mirror segment, whereby the secondary mirror segments differ in their curvatures or focal lengths, (e) the first primary mirror segment and the first secondary mirror segment are arranged in relation to each other such that a light beam is reflected back and forth between the two, and that (f) the second primary mirror segment and the second secondary mirror segment are arranged in relation to each other such that a light beam is reflected back and forth between the two.

Such a long path cell has the advantage that with the specified construction space, it provides a particularly long path route for the light beam. The background is that the segments can be constructed such that the distance in the circumferential direction of two adjacent points of contact does not essentially depend on the radial distance of the point of contact (i.e. on a radial coordinate). Thus, the segments can be formed such that the points of contact lie closely adjacent to each other.

The distances between the points of contact in the circumferential direction namely depend, with the given mirror distance, on the curvature of the respective mirror at the respective point of contact of the light beam. As a result, in the case of mirrors with a constant curvature, the distance between adjacent points of contact in the circumferential direction increases, the greater the radial distance between the points of contact. In order to make optimum use of the mirror surface available, the points of contact should be as closely adjacent to each other as possible. This is achieved through the differing curvatures in the case of spherically curved segments.

If at least one of the segments is parabolically curved, which is a preferred embodiment, the segments either differ in that they are parabolically or spherically curved, or—when two segments are parabolically curved—with regard to their focal lengths. It is particularly beneficial when all segments are parabolically curved.

The radial distance is the distance to an optical longitudinal axis of the long path cell. If, in a preferred embodiment, the light beam is reflected back and forth at least three times between the primary mirror and the secondary mirror, the points of contact of the light beam lie on a segment preferably along a circle, the middle point of which lies on the longitudinal axis.

Within the scope of the present description, a mirror is understood to be a device that, at least with regard to a wavelength, has a degree of reflection of at least 0.95, in particular 0.98.

The characteristic that the segments differ in their curvatures or focal lengths is understood in particular to mean that the function that describes the curvatures in the segments in dependence on the longitudinal axis is irregular on the boundaries of spatially adjacent segments. Alternatively, the segments are formed by annular or partially annular and/or spherical sections, in which the curvatures differ by at least 1 per thousand.

The point of contact is understood as being the point of the maximum intensity of the light beam. The light beam is preferably a laser beam.

In the case of spherically curved mirror segments, the curvature in the segment that lies radially further outwards is preferably larger than the adjacent segment that lies radially inwards. It is beneficial when the segments do not merge flush into each other. Preferably, at least for one segment, in particular for the majority of the segments, the segment that lies further inwards radially at the threshold between both segments is located axially closer to a middle point of the long path cell. This results in a compact structure.

In the case of parabolically curved mirror segments, the focal lengths preferably differ by at least one per thousand, in particular at least two per thousand.

One mirror segment is always either spherically curved, planar or parabolically curved. The mirrors are preferably arranged such that they create a constantly repeating self-centering and focusing of the light beam, and thus counteract an expansion of the light beam.

It is beneficial when at least one secondary mirror segment is planar. Planar means in particular non-curved, whereby one surface is considered as being non-curved when it has a curvature with a curvature radius of more than one kilometer. The maximum form deviation of a surface of a mirror segment in a point of contact is preferably less than $\lambda/2$, whereby $\lambda$ is the central vacuum wavelength of the light beam used, i.e. the one with the highest intensity.

According to a preferred embodiment, the primary mirror has a third primary mirror segment, which radially surrounds the second primary mirror segment, whereby the third primary mirror segment and the second primary mirror segment differ in their curvatures, whereby the secondary mirror has at least one third secondary mirror segment which radially surrounds the second secondary mirror segment, and whereby the third secondary mirror segment and the second secondary mirror segment differ in their curvatures. The third primary mirror segment and the third secondary mirror segment are arranged in relation to each other such that a light beam coupled into the long path cell is reflected back and forth between the two. Since the distance in the circumferential direction increases on a mirror segment of constant curvature with increasing radial distance, it is beneficial when each mirror has three or more mirror segments that are arranged in relation to each other such that a light beam is reflected back and forth between segments that are arranged in relation to each other. In the present case, the first primary mirror segment is arranged in relation to the first secondary mirror segment. Very generally, the ith primary mirror segment is arranged in relation to the ith secondary mirror segment, so that a light beam that is coupled into the long path cell is reflected back and forth between segments arranged in relation to each other.

The long path cell preferably comprises a reflection element that has a coupling-in area for coupling in a light beam into the long path cell and a decoupling area for decoupling the light beam from the long path cell, whereby the decoupling area runs at an offset angle of at least 30° to the decoupling area. It is beneficial when the coupling-in area and the decoupling area run almost at right-angles to each other. The angle between the coupling-in area and the decoupling area preferably deviates from 90° by at least 10 angle seconds.

It is particularly preferred that the reflection element has a first reflection area that is arranged such that a light beam that is coupled in from the coupling-in area is initially reflected by a mirror, in particular is reflected back and forth multiple times between mirror segments, then hits the first reflection area and in the beam path after the first reflection area hits another mirror segment of the same mirror. In this manner, the reflection element can deflect the light beams from one mirror segment onto an adjacent segment.

It is beneficial when the reflection element also has a second reflection area that guides the light beam onto one of the two third mirror segments.

The coupling-in element is preferably arranged between the mirrors. This is understood to mean in particular that the coupling-in element is arranged in the space of all points that lie on routes between the primary mirror and the secondary mirror.

Preferably, with transversal coupling in, the reflection element is designed such that a light beam decoupled from the decoupling area runs in an extension of a light beam that is coupled in by means of the coupling-in area. This should be understood in particular to mean that a distance that runs between a first straight line, along which the coupled-in light beam extends, and a second straight line, along which the decoupled light beam extends and which is measured on one plane which runs vertical to the first straight line, and the point of contact of the coupled-in light beam onto the coupling-in element, is at most 750 µm. Alternatively or in addition, the angle error between the first straight line and the second straight line is less than 0.5°.

Such a long path cell can, as already described above, be particularly simply inserted into the beam path of a device, such as a spectroscopy device.

Preferably, the first reflection area is therefore arranged to reflect the light beam, which falls from one segment with a first curvature onto the reflection area, onto a segment with a second curvature that differs from the first curvature.

Preferably, the non-planar segments are curved such that a distance in the circumferential direction between two adjacent points of contact on the same non-planar segment only differs by at most 50% from an average value of all distances in the circumferential direction between two adjacent points of contact. In other words, the distances in the circumferential direction between two adjacent points of contact are at least essentially the same. Preferably, this average value of all distances is at most ten times, in particular five times, as large as an average beam diameter of the light beams in the points of contact. The beam diameter is defined as the halfwidth (full width at half maximum). Thus, a particularly long path route can be realised in the long path cell. The beam diameter can change and always relates to the point at which the respective characteristic should apply.

According to a preferred embodiment, the long path cell comprises a holding element, whereby the primary mirror and the secondary mirror are affixed centrally on the holding element. The characteristic that the mirror is centrally affixed on the holding element is understood to mean that each mirror has a central area that lies radially inwards and that is connected to the mirror. In other words, the light beams run radially outside the holding element. It is beneficial when a longitudinal axis of the long path cells runs through the holding element.

It is beneficial when at least one of the primary mirror segments is planar over at least 75%, in particular at least 90%, of its area, at least one of the secondary mirror segments is planar over at least 75%, in particular 90%, of its area, the planar primary mirror segment is surrounded by a curved primary mirror segment and the planar secondary mirror segment is surrounded by a curved secondary mirror segment. In this case, the beam is frequently reflected back and forth between the planar mirror segments until the light beam hits the curved mirror segment.

It is possible, and is a preferred embodiment, that the primary mirror segment and/or the secondary mirror segment has an interchange section. This interchange section is inclined relative to the other area of the mirror segment such that a light beam that hits the interchange section is not reflected onto the mirror segment arranged in relation to it, but onto another mirror segment, such as a mirror segment that lies radially further outward.

Alternatively or in addition, it is possible that the long path cell has a relocation device that is arranged outside the convex sheath of the mirror. The convex sheath is the quantity of all those points that lie on a route, for which the end point of the straight lines lies on the primary mirror and the second end point lies on the secondary mirror. Preferably, for this purpose, at least one of the mirrors has a hole, so that the light beam can hit the relocation device and can be reflected by said device through the same hole or a second hole onto the other mirror. Here, the light beam is not reflected on the mirror segment that is arranged in relation to the mirror segment in which the hole is formed, but onto another mirror segment, such as a mirror segment that lies radially further outwards.

Additionally, according to the invention, a spectroscopy device with a long path cell such as the above cell is described.

The invention further resolves the problem through a long path cell, in particular a Herriott cell, with (a) a primary mirror, (b) a secondary mirror that faces towards the primary mirror with a concave mirror area, and (c) a coupling-in element that has a coupling-in area for coupling in a light beam and a decoupling area for decoupling the light beam, (d) whereby the decoupling area runs at an offset angle (a) of at least 30° to the coupling-in area, characterized in that (e) the coupling-in element has a first reflection area, which is arranged such that a light beam that is coupled in from the coupling-in area is initially reflected by at least one mirror, then hits the first reflection area and in the beam path after the first reflection area hits one of the mirrors, with which the decoupling areas run at an offset angle of at least 30° to the coupling-in area. The above preferred embodiments also relate to this invention. The preferred embodiments named below also relate to the inventions first named.

The advantage of this long path cell is that it can be produced such that there is no beam offset between the incidence beam and the outgoing beam. If such a long path cell is used in a spectroscopy device, for example, which has a laser and a detector, in particular a spectrometer, it is sufficient to insert the long path cell according to the invention into the beam path without the adjustment of the spectroscopy device being impaired relative to the laser. Such a spectroscopy device is a subject of the present invention.

Within the scope of the present description, a mirror is understood to be a device that, at least with regard to a wavelength, has a degree of reflection of at least 0.95, in particular 0.98.

The coupling-in element is understood to be an element that is arranged relative to the mirrors such that a light beam that hits the coupling-in element at a suitable angle is reflected onto the mirror, so that the light beam is reflected by this mirror onto the other mirror. The coupling-in element is also designed and arranged such that this light beam falls onto the decoupling area after several reflections and from there leaves the long path cell. The coupling-in element could therefore also be called a coupling-in and decoupling element.

The coupling-in element is preferably inserted between the mirrors. This is understood to mean in particular that the coupling-in element is arranged in the space of all points that lie on routes between the primary mirror and the secondary mirror.

Preferably, the secondary mirror is a spherical or parabolic mirror. These mirrors create a focusing and self-centering of the light beam, so that an expansion of the light beam is counteracted.

Preferably, the primary mirror also faces towards the secondary mirror with a concave mirror area. In this case, the primary mirror is preferably also a spherical and/or parabolic mirror.

Preferably, the coupling-in element is designed such that a light beam decoupled from the decoupling area runs in an extension of a light beam that is coupled in by means of the coupling-in area. This should be understood to mean in particular that a distance between a first straight line, along which the coupled-in light beam extends, and a second straight line, along which the decoupled light beam extends, is at most 750 µm, in particular at most 500 µm.

Preferably, the coupling-in element, which could also be called the coupling-in and deflection element, has a coating. It is beneficial when the distance between the two straight lines is preferably at most 1.4 times the thickness of the coupling-in element.

Alternatively or in addition, the angle error between the first straight line and the second straight line is less than 0.5°.

Such a long path cell can, as already described above, be particularly simply inserted into the beam path of a device, such as a spectroscopy device.

Preferably, the coupling-in element has a first reflection area, which is arranged such that a light beam that is coupled into the coupling-in area is initially reflected by at least one mirror, in particularly is reflected back and forth multiple times from the mirrors, then hits the first reflection area and in the beam path after the reflection area hits one of the mirrors. In other words, the light beam initially hits the coupling-in area and is reflected from there onto one of the mirrors. From this mirror, it is reflected onto the other mirror. It is possible, but not necessary, that the light beam is then reflected back and forth multiple times between the two mirrors. Then, the light beam hits the reflection area and is again reflected from there onto one of the mirrors. By means of such a coupling-in element, the light beam can be set onto a different track. In other words, several points of contact of the light beam lie before the contact on the coupling-in element along a first ellipsis, in particular of a first circle, and after the contact on the coupling-in element along a second ellipsis, in particular of a second circle.

Here, it is beneficial when a radial distance of a point of contact of the light beam that has been reflected onto one of the mirrors is significantly smaller or larger than the radial distance of the points of contact of the light beam before the reflection on the first reflection area. In other words, it is beneficial when the radial distances of the points of contact of the light beam before hitting the first reflection area essentially remain the same, and the reflection on the reflection area leads to the radial distance of the points of contact of the light beam being significantly smaller or significantly larger after reflection on the first reflection area. It is for example beneficial when the radial distance after reflection on the first reflection area differs by one radial offset from the radial distance of the point of contact of the light beam directly for hitting the first reflection area, whereby the radial offset is larger than double the variance of the radial distances of the points of contact of the light beam before it hits the reflection area.

The radial distance is the distance to an optical longitudinal axis of the long path cell. If, in a preferred embodiment, the light beam is reflected back and forth at least three times to the primary mirror and the secondary mirror, the points of contact preferably lie on ellipses, in particular circles, around the zero point of the radial axis.

One advantage of such a long path cell is that the light beam must cover a particularly long path length in the long path cell. The distances between the points of contact in the circumferential direction depend, in the case of the given mirror distance, on the curvature of the respective mirror. As a result, with mirrors with a constant curvature, the distance between adjacent points of contact in the circumferential direction increases, the greater the radial distance between the points of contact. In order to make optimum use of the mirror surface available, the points of contact should be as closely adjacent to each other as possible.

According to a further preferred embodiment, it is therefore provided that a curvature at least of one mirror, in particular of all mirrors, changes radially outward, in particular, becomes enlarged. After reflection through the coupling-in element, the points of contact then run on both mirrors on an ellipsis, in particular a circle. The points of contact of the light beam after hitting the first reflection area lie on a second ellipsis, in particular a second circle, which has a smaller or larger diameter, whereby the distances of the points of contact preferably do not differ, or do not differ significantly, in the circumferential direction on both ellipses.

Preferably, the coupling-in element comprises a second reflection area that is arranged relative to the coupling-in area such that a light beam that is coupled in from the coupling-in area is initially reflected back and forth by the mirrors multiple times, then hits the first reflection area, is then reflected back and forth by the mirrors multiple times, then hits the second reflection area, and is then again reflected back and forth by the mirrors multiple times.

Preferably, the points of contact of the light beam in its section between the first reflection area and the second reflection area lie on a first ellipsis, in particular a first circle. According to a preferred embodiment, the coupling-in element has a third reflection area, whereby the points of contact of the light beam in its section between the second reflection area and the third reflection area lie on a first ellipsis, in particular a second circle, which is at least essentially concentric to the first ellipsis, in particular to the first circle. The characteristic that the second ellipsis, in particular the second circle, is at least essentially concentric to the first ellipsis, in particular to the first circle, is in particular understood to be the fact that the focal points of the offset ellipses lie at a distance from each other of at most double a halfwidth of the light beam due to the respective points of contact. In the case of a circle, the middle points of the offset circles differ by at most double a halfwidth of the light beam due to the respective points of contact.

Preferably, the second ellipsis has a second total of a large and small half-axis, which differs from the first total of the large and small half-axis of the first ellipsis by at least one halfwidth of the light beam. In particular, the second circle preferably has a circle diameter that differs from the first circle diameter by at least double a halfwidth of the light beam.

Preferably, the first reflection area has a first partial area and a second partial area, whereby an opening angle between the two partial areas is at least 45°, in particular at least 60°, and/or at most 135°, in particular 120°. It is beneficial when the opening angle differs from 90° by at least 10 angle seconds.

According to a preferred embodiment, the long path cell comprises a holding element, whereby the primary mirror and the secondary mirror are affixed centrally on the holding element. The characteristic that the mirror is centrally affixed on the holding element is understood to mean that each mirror has a central area that lies radially inwards and that is connected to the mirror. In other words, the light beams run radially outside the holding element. It is beneficial when a longitudinal axis of the long path cells runs through the holding element. The holding element enables the alignment of the mirrors in relation to each other. Thus, at least one mirror can be affixed on the holding element in an arrestable manner with regard to longitudinal movement, so that the mirror can initially be moved and then arrested relative to the holding element. Alternatively or in addition, the holding element also preferably comprises an angle position setting device, by means of which the angle position at which at least one of the mirrors is affixed relative to the holding element is adjustable.

Additionally, according to the invention, a spectroscopy device with a long path cell such as the above cell is described.

The invention will be explained in greater detail below with reference to the appended drawings, in which:

FIG. 6 shows a further long path cell according to the invention in FIG. 6a, in which the inner pair of mirror segments arranged in relation to each other is planar with a first part of the beam path, and the FIG. 6b shows a schematic view of the complete beam path.

Figure 1:
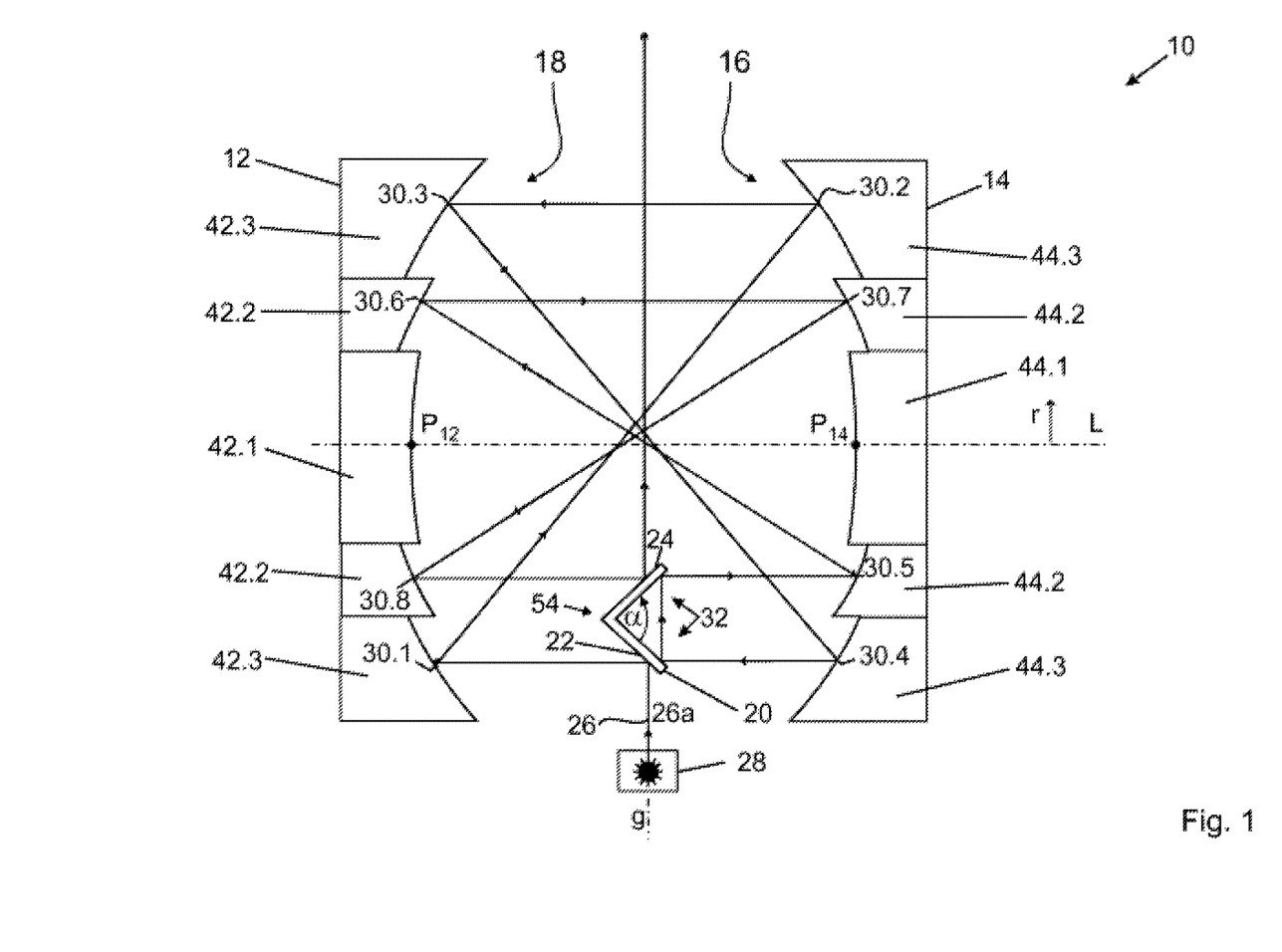
FIG. 1 shows a schematic cross-section through a long path cell according to one embodiment of the invention.

FIG. 1 shows a long path cell 10 according to the invention in the form of a Herriott cell, which has a primary mirror 12 and a secondary mirror 14. The primary mirror 12 has a primary mirror area 16, the secondary mirror 14 has a secondary mirror area 18, which faces towards the primary mirror 12. The primary mirror 12 is in the present case spherical in sections and has a first curvature radius $R_{12}(r)$, which, for each radial distance r, corresponds to a second curvature radius $R_{14}(r)$ of the secondary mirror.

However, it is also possible that one or both mirrors are entirely, or in sections, parabolic mirrors. In this case, too, the curvature radius of a mirror for each radial distance r preferably corresponds to the second curvature radius $R_{14}(r)$ of the secondary mirror.

The long path cell 10 comprises a reflection element 54, which has a coupling-in-area 22 and a decoupling area 24. The section of the reflection element 54 on which the coupling-in area 22 and the decoupling area 24 are formed can be referred to as the coupling-in element 20.

If a light beam 26, in particular a laser beam, which is emitted from a laser 28, falls onto the coupling-in area 22, this reflects the light beam 26 on to the primary mirror 12. The light beam 26 therefore initially hits the primary mirror 12 in a first point of contact 30.1. Then, the primary mirror 12 reflects the light beam 26 onto a second point of contact 30.2 on the secondary mirror 14, then the light beam 26 hits a third point of contact 30.3 and a fourth point of contact 30.4.

The light beam 26 is in other words reflected back and forth multiple times by the mirrors 12, 14. Then—or after further reflections on the mirrors—the light beam 26 hits a first reflection area 32, which guides the light beam 26 onto a fifth point of contact 30.5 on the secondary mirror area 18. In the present case, the first reflection area 32 extends along two planes that run vertical in relation to each other.

After the laser beam has run through the points of contact 30.6, 30.7 and 30.8, it hits the decoupling area 24. The outgoing light beam 26b that is created, which is a section of the light beam 26, runs in the direct extension of the incident section 26a of the light beam 26. In other words, a straight line g exists, along which both the incident light beam 26*a* and the outgoing light beam 26*b* extend.

It can be seen that the decoupling area 24 is oriented to the coupling-in area 22 at an offset angle α. In the present case, α=90°, which is a possible embodiment with the two-dimensional beam path. However, it is particularly beneficial when the offset angle with the usually occurring three-dimensional beam path differs from 90° by at least 10 arc seconds.

The long path cell 10 has a longitudinal axis L. The longitudinal axis L runs through the two points $P_{12}$, $P_{14}$, which are characterized by the fact that a conceived light beam between these two points would be constantly reflected back and forth.

In a circle coordination system around the longitudinal axis L, the distance coordinate r is measured starting from the longitudinal axis L. The z-coordinates in this coordinate system can in general be selected as required, although preferably, z=0 on the point at which the longitudinal axis L lies, and which lies precisely between points $P_{12}$ and $P_{14}$.

It should be noted that FIG. 1 merely shows a schematic side view of the long path cell 10. It is possible for both mirrors to have a greater distance from each other.

As FIG. 1 shows, the primary mirror 12 has a first primary mirror segment 42.1, a second primary mirror segment 42.2 and a third primary mirror segment 42.3. The second primary mirror segment 42.2 radially surrounds the first primary mirror segment 42.1. The third primary mirror segment 42.3 radially surrounds the second primary mirror segment 42.2. Segments 42.1, 42.2, 42.3 are spherically curved and differ with regard to their curvatures and/or focal lengths. Thus the curvature radius $R_{42.1}$ of the first primary mirror segment 42.1 is larger than the curvature radius $R_{42.2}$ of the second primary mirror segment 42.2. In this embodiment, the curvature radius R becomes smaller, the larger the distance r between the respective segment and the longitudinal axis L. However, embodiments are also possible in which the curvature radius R at least does not always become smaller, the greater the distance r between the respective segment and the longitudinal axis L.

A secondary mirror segment 44.*i* (i=1, 2, etc.) is arranged in relation to each primary mirror segment 42.*i*. The light beam 26 is in this embodiment reflected back and forth between the pair consisting of the primary mirror segment 42.*i* and the secondary mirror segment 44.*i* arranged in relation to each other, until it hits a reflection area or the decoupling area 24.

The incident light beam 26*a* first hits the coupling-in area 22 and then, after passing through the points of contact 30.1, 30.2, 30.3 and 30.4, it hits the first reflection area 32. In the beam path after the first reflection area 32, the light beam 26 then hits the primary mirror 12 in the fifth point of contact 30.5. After passing through the points of contact 30.6, 30.7 and 30.8, the light beam 26 hits the decoupling area 24 and is decoupled from the long path cell 10. Naturally, it is possible, and is a preferred embodiment, that the coupling-in element 20 has further reflection areas. In this case, it is advantageous when the primary mirror 12 and/or the secondary mirror 14 has additional segments.

FIG. 1 shows that the first reflection area 32 serves to relocate the light beam from one segment to the next. The segments—as represented in a preferred embodiment—are designed such that the light beam 26 is constantly reflected back and forth between the same pair of mirror segments consisting of the primary mirror segment and the secondary mirror segment arranged in relation to each other, until it hits a reflection area. Then, the light beam runs solely on a second pair consisting of the primary mirror segment and the secondary mirror segment, until it either hits the decoupling area or a further reflection area.

Figure 2:
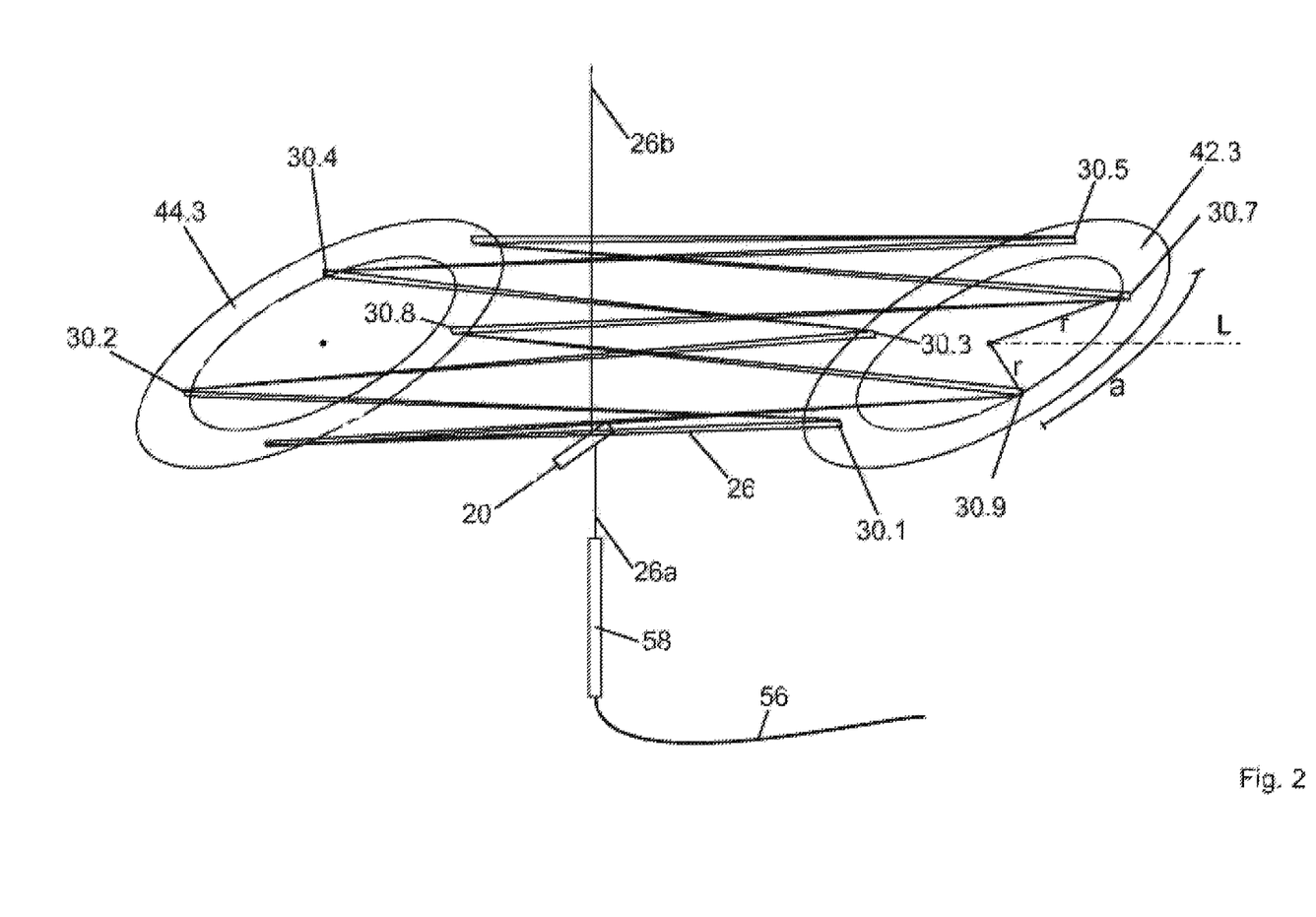
FIG. 2 shows a schematic view that illustrates the path of the light beam.

FIG. 2 shows a schematic view of the beam path of the light beam 26, which it completes between the segments 42.3 and 44.3. A distance a in the circumferential direction between adjacent points of contact, such as between the points of contact 30. 39.7 or 30.9 and 30.1, is constant as a good approximation. A radial distance r is essentially the same for each point of contact. In other words, $r_{30.7}=r_{30.9}$, whereby two distances are considered to be essentially the same when the distances differ by less than 25%.

For a segment that lies further inward radially, in the present case for the primary mirror segment 42.2 and the secondary mirror segment 44.2, the distance a in the circumferential direction is also preferably essentially the same between adjacent points of contact.

The long path cell 10 is designed such that the distance a in the circumferential direction of two adjacent points of contact is larger than double the halfwidth of the light beam. Preferably, this distance is additionally smaller than 20 times, in particular than 10 times, the halfwidth breadth. In order to be able to maintain these framework conditions independently of the segment, the curvatures of the individual segments 42.*e*, 44.*i* differ for different i.

FIG. 2 shows that the long path cell 10 can have an optical fibre 56, in which the light beam 26 is guided by the laser 28 onto the coupling-in element 20. It is beneficial when the optical fibre 56 ends in a decoupling element 58.

Figure 3:
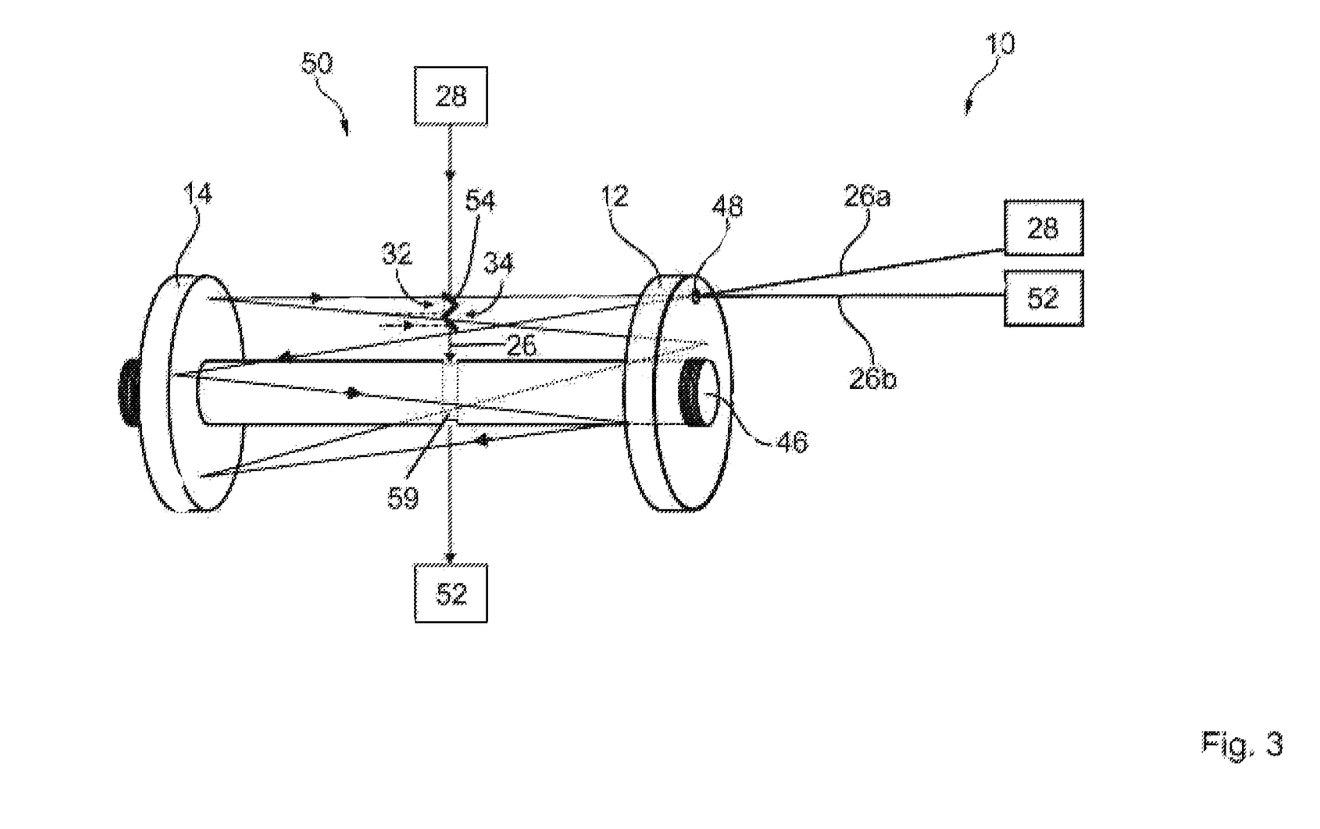
FIG. 3 shows a further embodiment of a long path cell according to the invention.

FIG. 3 shows a further embodiment of a long path cell 10 according to the invention, in which the mirrors 12, 14 are structured as shown in FIG. 1. The long path cell 10 comprises a holding element 46, on which the two mirrors 12, 14 are centrally affixed. It can be seen that the light beam 26 enters into the long path cell 10 through an opening 48 in the mirror 12 and exits again through the same opening 48.

An independent invention is also a spectroscopy device 50 that has the laser 28, the long path cell 10 and a light beam analysis device 52.

FIG. 3 also shows a schematic view of the reflection element 54, on which the reflection areas 32 and 34 are formed. With the embodiments according to FIGS. 1 and 2, the reflection element is a part of the coupling-in element 20 (see FIG. 1). For the sake of clarity, in FIG. 3, the beam paths after reflection on the first reflection area 32 and the second reflection area 34 are only drawn in schematically. In this case, the light beam 26 is for example decoupled through a hole 59 in the holding element 46. Alternatively, the detection device 52 can also be affixed on the holding element 46 or contained within it.

Figure 4:
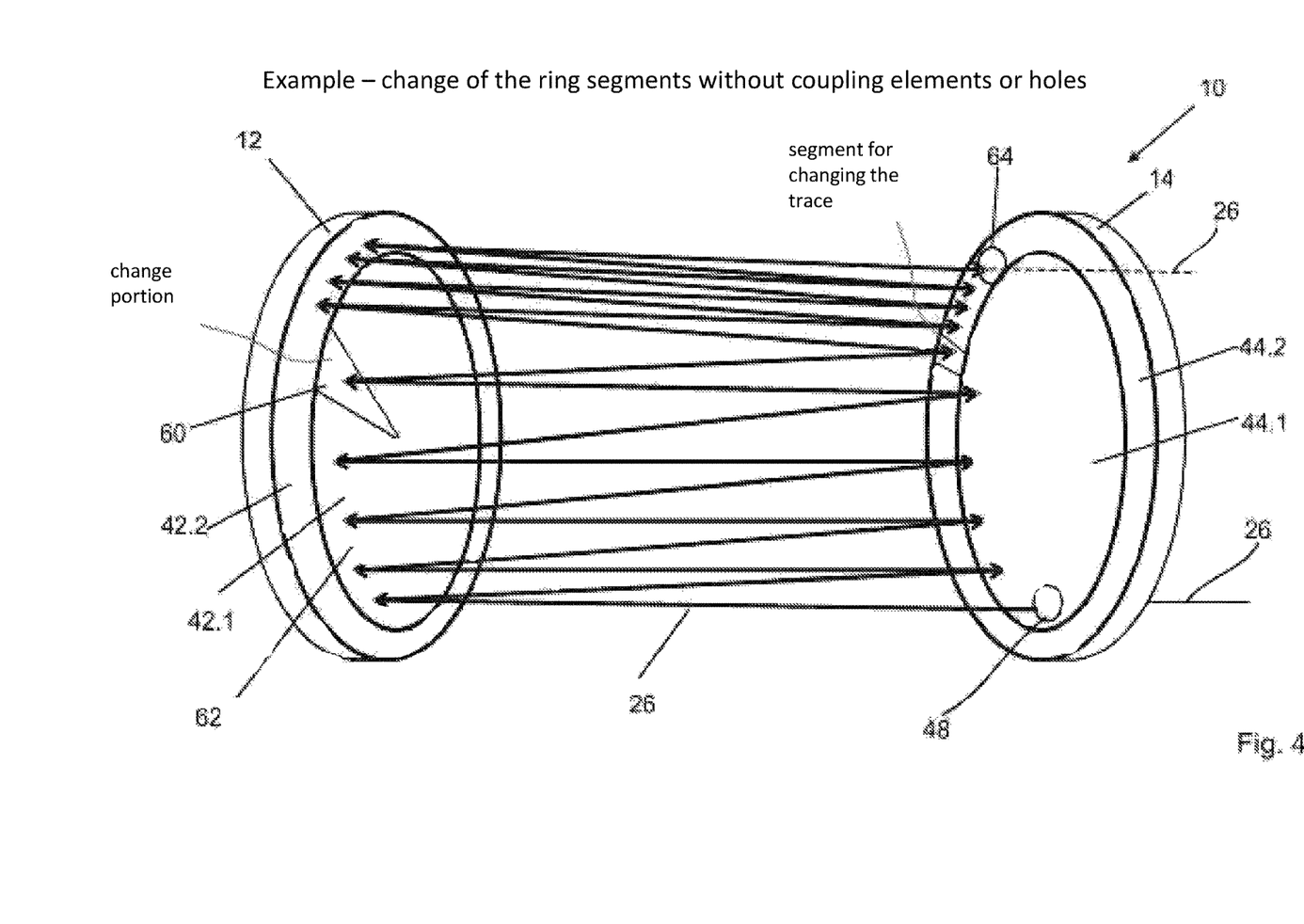
FIG. 4 shows a further embodiment of a long path cell according to the invention, in which the change between two segments is realised by a triangular partial piece of the inner segment and a partial piece of the outer segment that is then hit by the light beam.

FIG. 4 shows a second embodiment of a long path cell 10 according to the invention, in which the light beam 26 conducts a complete rotation. Alternatively, it is possible that the light beam 26 is coupled into the long path cell 10 through the opening 48. The first primary mirror segment 42.1 is formed from a transition section 60 and a mirror area 62. The mirror area 62 is spherically curved. The first secondary mirror segment 44.1 arranged in relation is also spherically curved and is aligned parallel to the mirror area 62. Light that hits the mirror area 62 is reflected onto the first secondary mirror segment 44.1. If the light beam 26 hits the transition section 60, it is reflected onto the second secondary mirror segment 44.2. From there, it is reflected onto the second primary mirror segment 42.2. Through a second opening 64, the light beam 26 is again decoupled from the long path cell 10.

Alternatively, it is possible that a section of a mirror segment, similar to the transition section 60, is formed such that the light beam 26 can be coupled in at the side.

Figure 5:
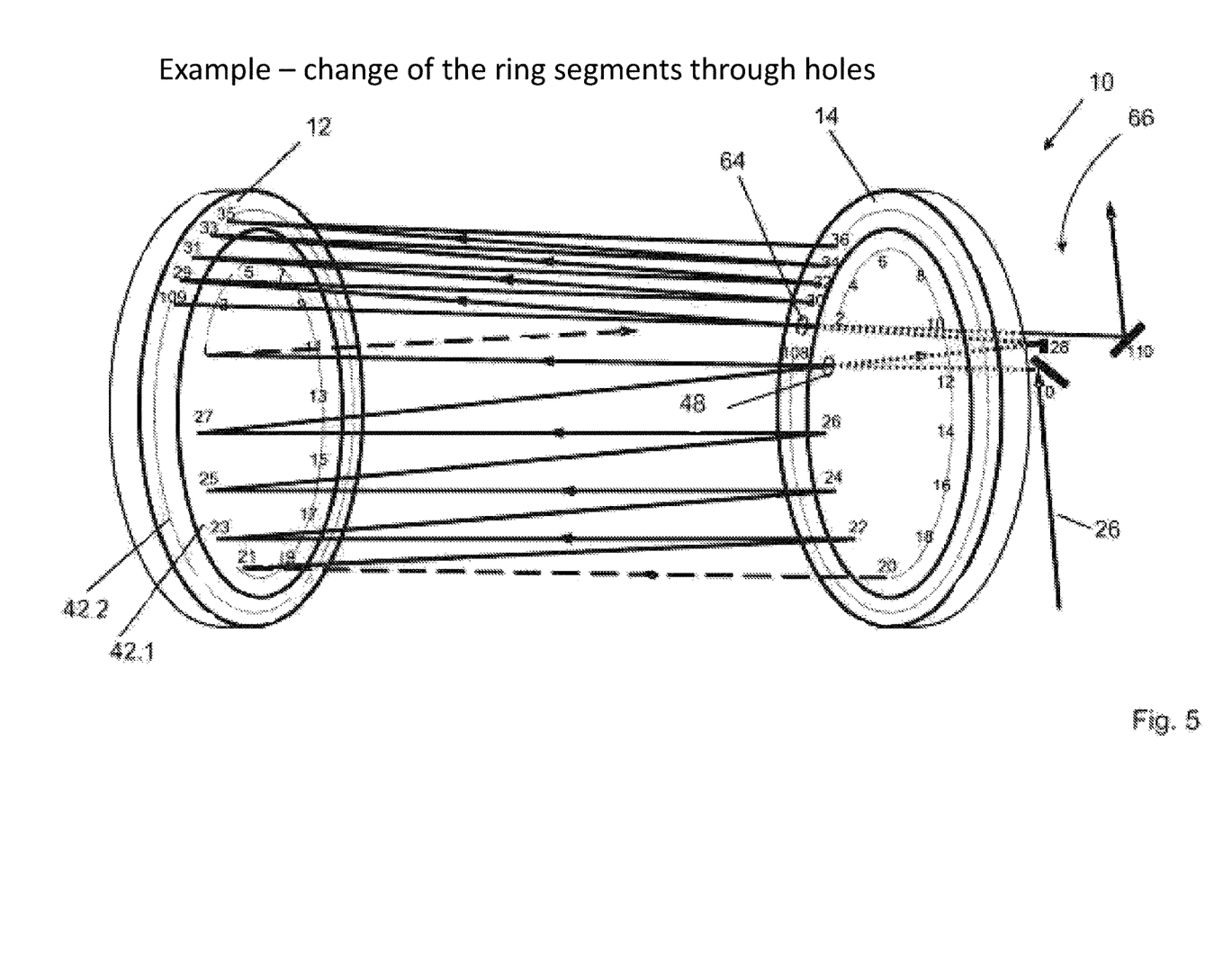
FIG. 5 shows a further long path cell according to the invention with a relocation device for relocating the light beam from a pair of mirror segments onto a second pair of mirror segments.

FIG. 5 shows a further long path cell 10 according to the invention, which has a relocation device 66. This relocation device is arranged outside the volume between the mirrors 12, 14 and reflects the light beam from one primary mirror segment onto another. The numbers adjacent to the points of contact enumerate the points of contact so that the beam path is easier to follow. It can be seen that the light beam 26 is coupled in through the opening 48 and decoupled through the second opening 64.

Figures 6A, 6B:
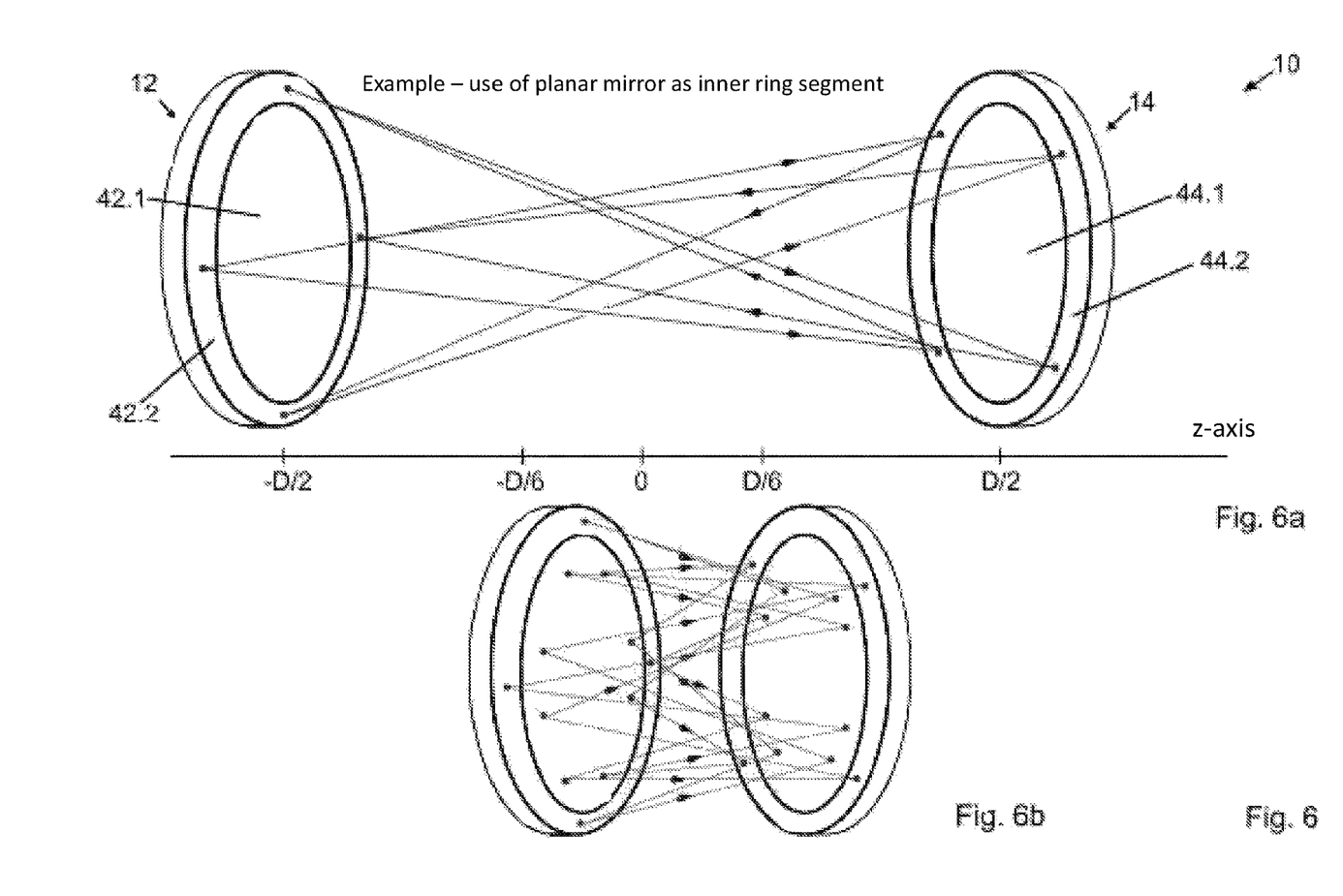

FIG. 6 shows a schematic view in the FIGS. 6a and 6b of the beam path for a long path cell 10, in which the first primary mirror segment 42.1 and the first secondary mirror segment 44.1 are planar and that the second primary mirror segment 42.2 and the second secondary mirror segment 44.2 are spherically curved.

FIG. 6a shows the case in which the distance between the two mirrors 12, 14 is so large that the beam path corresponds to that of a Herriott cell.

FIG. 6b shows the beam path when the distance between the two mirrors 12, 14 is so small (here: one-third of the distance according to FIG. 6a) that significantly more reflections occur. The positions of the points of contact on 44.1 correspond to the beam positions in the cross-section at z=−⅙ D (mirror distance from FIG. 6a). The positions of the points of contact on 42.1 correspond to the beam positions in the cross-section at z=+⅙ D. The number of reflections on the inner planar segments is in this case double those on the outer curved segments. If the mirrors are pushed closer together, so that the distance is equal to D/(2N+1), whereby N is a natural number, the number of reflections on the inner planar segments is 2N times larger than on the outer curved segments. Thus, for example, 100 reflections could be realised on the outer segment, and with one-thirteenth of the mirror distance calculated for the standard Herriott cell or similar to thirteen times the curvature radius of the mirrors, 12×100=1,200 reflections would be obtained on the planar mirrors, and thus 1,300 reflections in total. With a mirror distance of just approximately 77 cm, an optical path length is thus achieved of over one kilometer, with simultaneous maintenance of the beam properties and robustness as is common for the standard Herriott cell.

Figure 7:
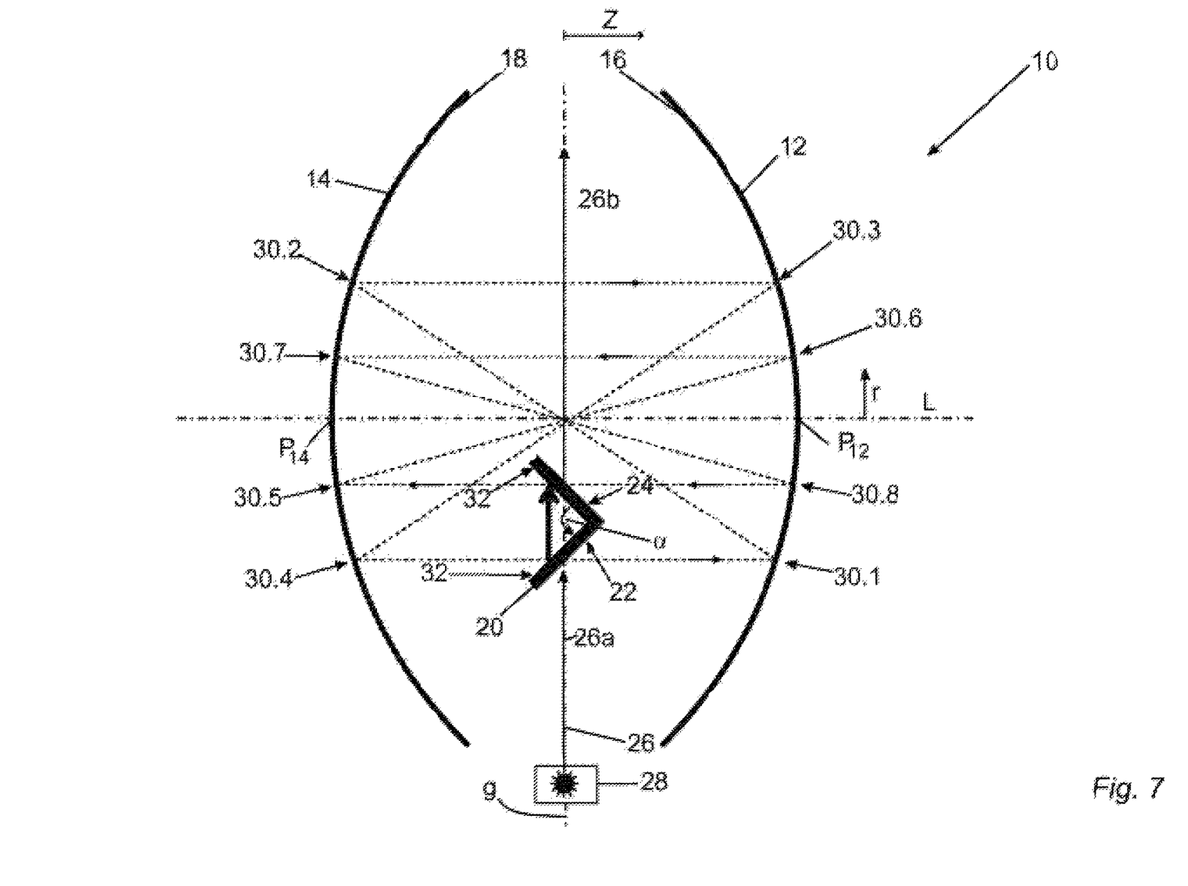
FIG. 7 shows a long path cell according to the invention according to a further embodiment of the invention.

FIG. 7 shows a long path cell 10 according to the invention in the form of a Herriott cell, which has a primary mirror 12 and a secondary mirror 14. The primary mirror 12 has a first concave mirror area 16, the secondary mirror 14 has a secondary mirror area 18, which faces towards the primary mirror 12. The primary mirror 12 is in the present case spherical and has a first curvature radius $R_{12}$, which corresponds to a second curvature radius $R_{14}$ of the secondary mirror. However, it is also possible that one or both mirrors are parabolic mirrors.

The long path cell 10 comprises a coupling-in element 20, which has a coupling-in area 22 and a decoupling area 24. If a light beam 26, in particular a laser beam, which is emitted from a laser 28, falls onto the coupling-in area 22, this reflects the light beam 26 on to the primary mirror 12. The light beam 26 therefore initially hits the primary mirror 12 in a first point of contact 30.1. Then, the primary mirror 12 reflects the light beam 26 onto a second point of contact 30.2 on the secondary mirror 14, then the light beam 26 hits a third point of contact 30.3 and a fourth point of contact 30.4.

The light beam 26 is in other words reflected back and forth multiple times by the mirrors 12, 14. Then the light beam 26 hits a first reflection area 32, which guides the light beam 26 onto a fifth point of contact 30.5 on the secondary mirror area 18. In the present case, the first reflection area 32 extends along two planes, which form an angle with each other that is not a right angle. In the two-dimensional case shown schematically, a right angle would result, which is however not present in the three-dimensional case.

After the laser beam has run through the points of contact 30.6, 30.7 and 30.8, it hits the decoupling area 24. FIG. 7 shows a side view, so that the light beam is drawn running virtually parallel between the points 30.4 and 30.5 on the one hand, and behind the point 30.8 on the other. The outgoing light beam 26b, which is a part of the light beam 26, runs into the direct extension of the incident light beam 26a. In other words, a straight line g exists, along which both the incident light beam 26a and the outgoing light beam 26b extend.

It can be seen that the decoupling area 24 is oriented to the coupling-in area at an offset angle α. In the present case, α=90°, which is a preferred embodiment solely for the two-dimensional case. For the three-dimensional case, which occurs in practice, α must differ from 90°, so that good adjustment is made possible, which is characterized by rotational symmetry or by the circular arrangement of the points of contact on the mirrors. For each set of input parameters: "Curvature radii (focal lengths) of the mirrors, the mirror distance, the position of the coupling-in element, the radius of the current (prior to deflection onto the next track) circular pattern of the reflexes on the mirrors, the radius of the next (emerging on the new track) circular pattern of the reflexes on the mirrors" there are precisely two possible angles for α, the size of which is determined according to the invention by means of a simulation using raytracing.

The long path cell 10 has a longitudinal axis L. In the present case, the longitudinal axis runs through the two points $P_{12}$, $P_{14}$, which are characterized by the fact that a conceived light beam between these two points would be constantly reflected back and forth. In a cross-section view as shown in FIG. 7, the longitudinal axis is a rotational symmetry axis for the primary mirror 12. Additionally, the mirror surfaces 16, 18 can be shown in a circle coordinate system around the longitudinal axis L as a constant in a distance coordinate r. The distance coordinate r designates the distance from the longitudinal axis L. The z-axis runs along the longitudinal axis L. The point Z=0 can generally be selected as required.

It should be noted that FIG. 7 merely shows a schematic side view of the long path cell 10. For this reason, the angles drawn in are shown as distorted. It is possible for both mirrors to have a greater distance from each other.

Figure 8A:
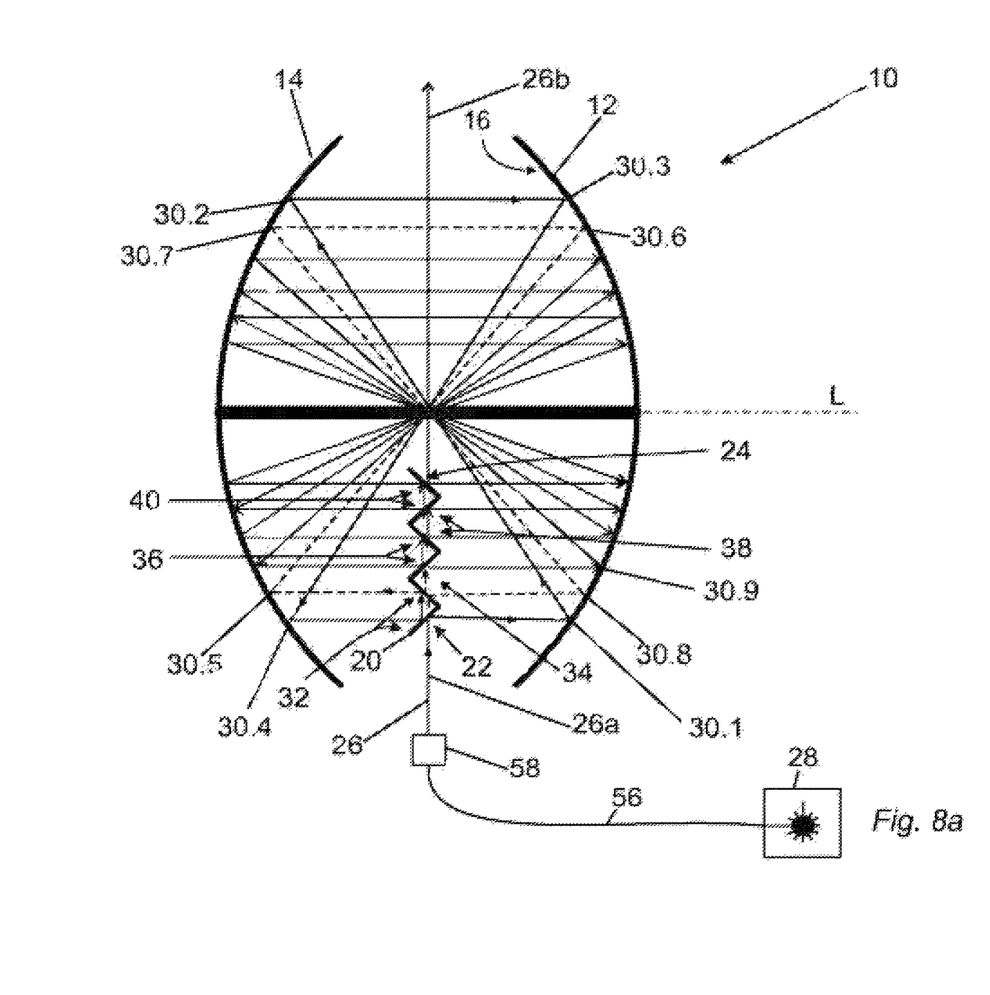
FIG. 8a shows a schematic view of a long path cell according to a further embodiment of the invention.

FIG. 8a shows a second embodiment of a long path cell 10 according to the invention, the coupling-in element 20 of which has a second reflection area 34 which the light beam 26 hits, after it has been reflected in the point of contact 30.8. The second reflection area 34 reflects the light beam 26 onto the point of contact 30.9. The coupling-in element 20 also has a third reflection area 36, a fourth reflection area 38 and a fifth reflection area 40. As can be seen from the path of the light beam 26 that has been drawn in, said light beam completes a particularly long path in the long path cell 10.

FIG. 8a shows that the long path cell 10 can have an optical fibre 56, in which the light beam 26 is guided by the laser 28 onto the coupling-in element 20. It is beneficial when the optical fibre 56 ends in a decoupling element 58.

Figure 8B:
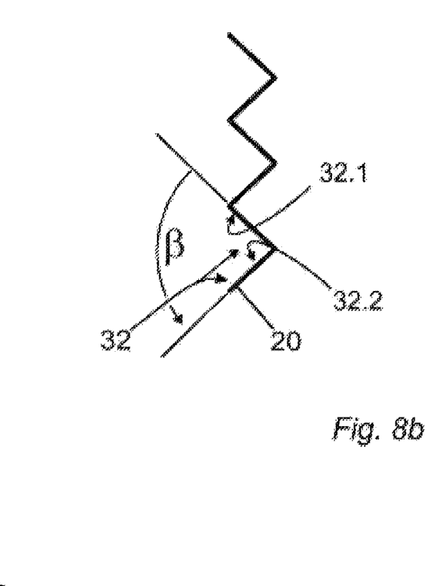
FIG. 8b shows a cross-section with the coupling-in element from the long path cell shown in FIG. 8a, FIG. 9 shows a schematic cross-section through a long path cell according to a further embodiment of the invention.

FIG. 8b shows the coupling-in element 20 in an enlargement. It can be seen that the first reflection area 32 has a first partial area 32.1 and a second partial area 32.2, which with the first area 32.1 incorporates an opening angle β. The opening angle β is in each case the angle between the two tangential planes on the areas 32.1, 32.2 at the point in which the light beam 26 hits.

The opening angle β between the two partial areas 32.1, 32.2 is preferably at least 45°, in particular at least 60°, and/or at most 135°, in particular 120°. It has been shown to be advantageous when the opening angle β has a value between 89°, preferably 89.5°, on the one hand, and 90.5°, preferably 91°, on the other.

For the partial areas, there are always precisely two possible orientations to each other, in which the profile of the pattern of the light beam reflections is as circular as possible. Preferably, this orientation is determined by means of ray-tracing.

Figure 9:
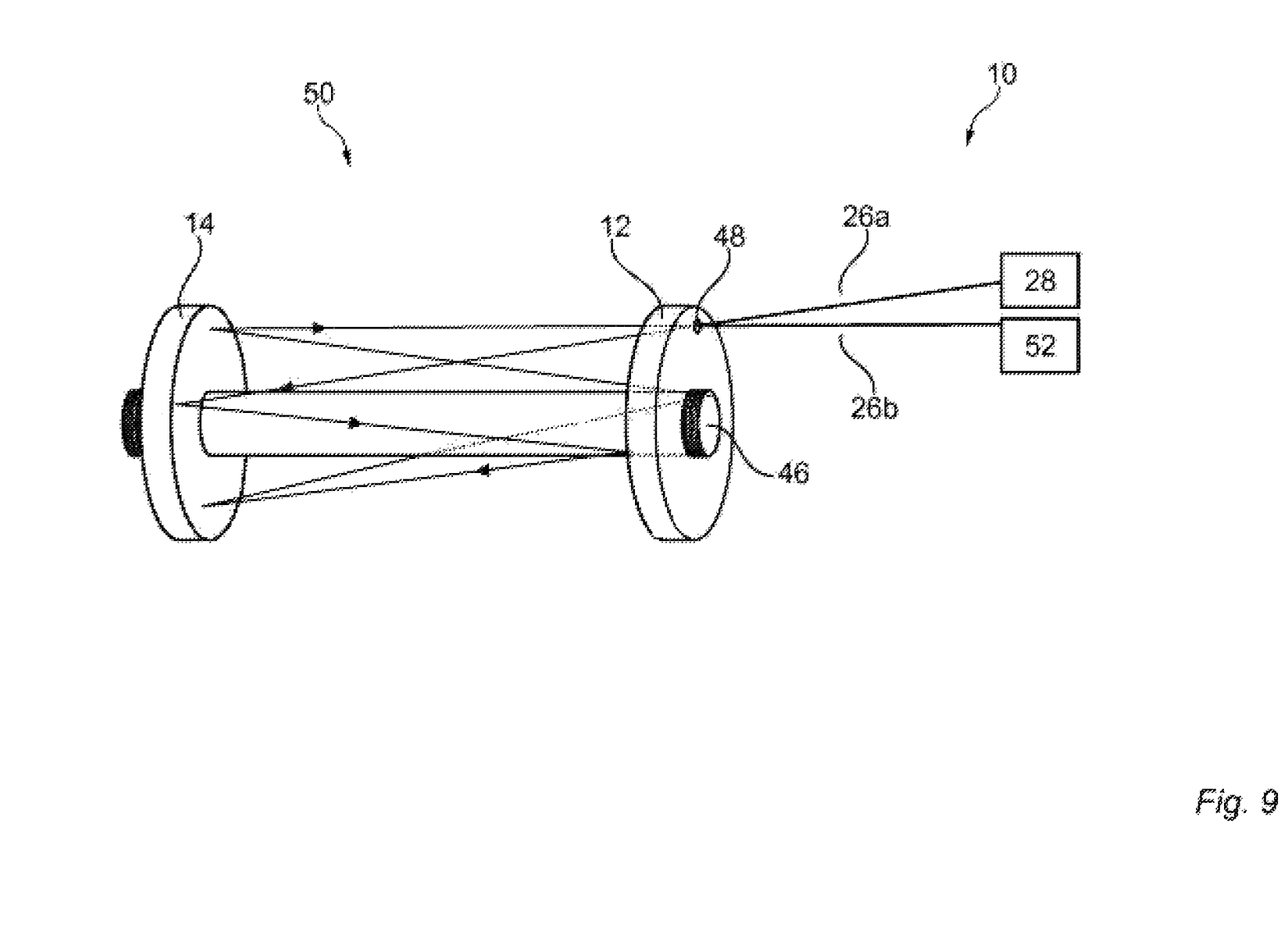

FIG. 9 shows a further embodiment of a long path cell 10 according to the invention, in which the mirrors 12, 14 are structured as shown in FIG. 9. The long path cell 10 comprises a holding element 46, on which the two mirrors 12, 14 are centrally affixed. It can be seen that the light beam 26 enters into the long path cell 10 through an opening 48 in the mirror 12 and exits again through the same opening 48.

The invention also provides a spectroscopy device 50 that has the laser 28, the long path cell 10 and a light beam analysis device 52.

Figure 10:
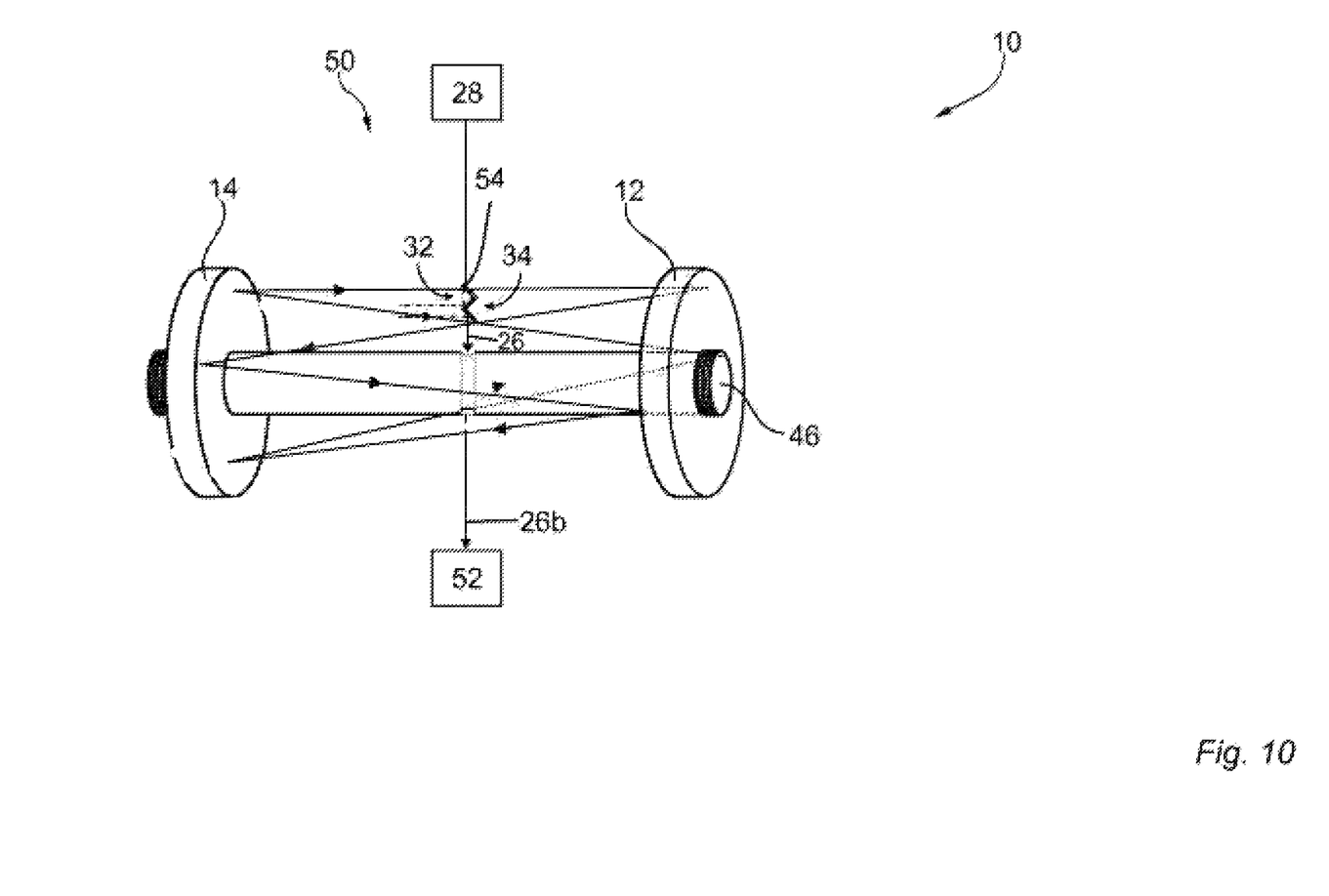
FIG. 10 shows a further embodiment of a long path cell according to the invention.

FIG. 10 shows a further embodiment of a long path cell 10 according to the invention with a reflection element 54 on which the reflection areas 32 and 34 are formed. With the embodiments according to FIGS. 1 and 2, the reflection element is a part of the coupling-in element 20 (see FIG. 7).

For the sake of clarity, in FIG. 10, the beam path after reflection on the first reflection area 32 and the second reflection area 34 is only drawn in schematically.

| List of reference numerals | |
|---|---|
| 10 | Long path cell |
| 12 | Primary mirror |
| 14 | Secondary mirror |
| 16 | Primary mirror area |
| 18 | Secondary mirror area |
| 20 | Coupling-in element |
| 22 | Coupling-in area |
| 24 | Decoupling area |
| 26 | Light beam |
| 26a | Outgoing light beam |
| 26b | Incident light beam |
| 28 | Laser |
| 30 | Point of contact |
| 32 | First reflection area |
| 32.1, 32.2 | Partial area |
| 34 | Second reflection area |
| 36 | Third reflection area |
| 38 | Fourth reflection area |
| 40 | Fifth reflection area |
| 42 | Primary mirror segment |
| 44 | Secondary mirror segment |
| 46 | Holding element |
| 48 | Opening |
| 50 | Spectroscopy device |
| 52 | Light beam analysis device |
| 54 | Reflection element |
| 56 | Optical fibre |
| 58 | Decoupling element |
| 60 | Transition section |
| 62 | Mirror area |
| 64 | Opening |
| 66 | Relocation device |
| α | Offset angle |
| β | Opening angle |

-continued

| List of reference numerals | |
|---|---|
| a | Distance |
| g | Straight line |
| L | Longitudinal axis |
| r | Distance coordinate |
| R | Curvature radius |
| $R_{12}$ | Curvature radius |
| $R_{14}$ | Curvature radius |
| $R_{42.1}$ | Curvature radius |
| D | Mirror distance initial value |

The invention claimed is:

1. A long path cell (10), in particular a Herriott cell, with
(a) a primary mirror (12) and
(b) a secondary mirror (14),
characterized in that
(c) the primary mirror (12) has
   a first primary mirror segment (42.1) and
   at least one second primary mirror segment (42.2), which radially surrounds the first primary mirror segment (42.1),
   whereby the primary mirror segments (42) differ in their curvatures ($R_{42.1}$, $_{42.2}$) or focal lengths,
(d) the secondary mirror (14) has
   a first secondary mirror segment (44.1) and
   at least one second secondary mirror segment (44.2) which radially surrounds the first secondary mirror segment (44.1),
   whereby the secondary mirror segments (44) differ in their curvatures ($R_{42.1}$, $R_{42.2}$) or focal lengths,
(e) the first primary mirror segment (42.1) and the first secondary mirror segment (44.1) are arranged in relation to each other such that a light beam is reflected back and forth between the two, and that
(f) the second primary mirror segment (42.2) and the second secondary mirror segment (44.2) are arranged in relation to each other such that a light beam is reflected back and forth between the two.

2. The long path cell (10) according to claim 1, characterized in that
(a) the primary mirror (12)
   has a third primary mirror segment (42.3), which radially surrounds the second primary mirror segment (42.2),
   whereby the third primary mirror segment (42.4) and the second primary mirror segment (42.2) differ in their curvatures ($R_{42.3}$, $R_{42.2}$) or focal lengths,
(b) the secondary mirror (14)
   has at least one third secondary mirror segment (44.3) which radially surrounds the second secondary mirror segment (44.2),
   the third secondary mirror segment (44.3) and the second secondary mirror segment (44.2) differ in their curvatures ($R_{44.3}$, $R_{44.2}$) or focal lengths, and that
(c) the third primary mirror segment (42.3) and the third secondary mirror segment (44.3) are arranged in relation to each other such that a light beam is reflected back and forth between the two.

3. The long path cell (10) according to claim 1, characterized by a reflection element (54) that has
   a coupling-in area for coupling in a light beam (26) into the long path cell (10) and
   a decoupling area (24) for decoupling the light beam (26) from the long path cell (10), whereby the decoupling area (24) runs at an offset angle (α) of at least 30° to the coupling-in area (22).

4. The long path cell (10) according to claim 3, characterized in that the reflection element (54)
has a first reflection area (32) that is arranged such that a light beam (26) that is coupled in from the coupling-in area (22)
is initially reflected by at least one mirror segment (44.3), in particular is reflected back and forth multiple times between mirror segments (42.3, 44.3), then hits the first reflection area (32), and
in the beam path after the first reflection area (32), hits another mirror segment (42.2) of the same mirror.

5. The long path cell (10) according to claim 4, characterized in that the reflection element (54)
has a second reflection area (34) that is arranged relative to the coupling-in area (22) such that a light beam (26) that is coupled in from the coupling-in area (22), which has been reflected from the first reflection area (32) onto a mirror segment, is reflected onto a mirror segment that it has not yet hit in the previous beam path.

6. The long path cell (10) according to claim 5, characterized in that the first reflection area (32) is arranged to reflect a light beam (26) which falls from a mirror segment with a first curvature ($R_{42.1}$) or a first focal length onto the reflection area (32) onto a segment with a second curvature ($R_{42.2}$) or focal length that differs from the first curvature ($R_{42.1}$).

7. The long path cell (10) according to claim 4, characterized in that
the first reflection area (32) is arranged to reflect a light beam (26) which falls from a mirror segment with a first curvature ($R_{4.21}$) or a first focal length onto the reflection area (32) onto a segment with a second curvature ($R_{42.2}$) or focal length that differs from the first curvature ($R_{42.1}$).

8. The long path cell (10) according to claim 1, characterized in that
at least one of the primary mirror segments (42.1) is planar over at least 75%, in particular at least 90%, of its area,
at least one of the secondary mirror segments (44.1) is planar over at least 75%, in particular at least 90%, of its area
the planar primary mirror segment (42.1) is surrounded by a curved primary mirror segment (42.2), and
the planar secondary mirror segment (44.1) is surrounded by a curved secondary mirror segment (44.2).

9. The long path cell (10) according to claim 1, characterized by
a holding element (46),
whereby the primary mirror (12) and the secondary mirror (14) are centrally affixed on the holding element (46).

10. The long path cell (10) according to claim 1, characterized by at least one third, planar mirror that is arranged such that a light beam (26) hits all mirrors before it leaves the long path cell (10).

11. The long path cell (10) according to claim 1, characterized by an optical fibre (56), which is arranged to guide the light beam (26) and is arranged such that the light beam (26) can be coupled into the long path cell (10).

12. The long path cell (10) according to claim 1, characterized in that
(a) the secondary mirror (14) faces towards the primary mirror (12) with a concave mirror area (18), in that
(b) the long path cell has a coupling-in element (20), which has
a coupling-in area (22) for coupling in a light beam (26) and
a decoupling area (24) for decoupling the light beam (26),
(c) whereby the decoupling area (24) runs at an offset angle (a) of at least 30° to the coupling-in area (22), in that
(d) the coupling-in element (20) has a first reflection area (32), which is arranged such that a light beam (26) coupled in from the coupling-in area (22)
is initially reflected from at least one mirror (12), then hits the first reflection area (32), and
in the beam path after the first reflection area (32), hits one of the mirrors (12, 14).

13. The long path cell (10) according to claim 12, characterized in that the coupling-in element (20) is formed such that a light beam (26b) decoupled from the decoupling area (24) runs in an extension of a light beam (26a) that is coupled in by means of the coupling-in area (22).

14. The long path cell (10) according to claim 12, characterized in that
the coupling-in element (20) has a second reflection area (34), which is arranged relative to the coupling-in area (22) such that a light beam (26) that is coupled in from the coupling-in area (22)
is reflected back and forth multiple times by the mirrors (12, 14),
then hits the second reflection area (34), and
is subsequently reflected back and forth multiple times by the mirrors (12, 14).

15. The long path cell (10) according to claim 12, characterized in that the first reflection area (32) has a first partial area (32.1) and a second partial area (32.2), whereby an opening angle (□) between the two partial areas (32.1, 32.2) is at least 45° and/or at most 135°.

16. The long path cell (10) according to claim 1, characterized by at least one third, concave mirror, which is arranged such that a light beam (26) hits all mirrors before it leaves the long path cell (10).

* * * * *